United States Patent [19]
Maryanoff et al.

[11] 4,210,590
[45] Jul. 1, 1980

[54] REDUCTION OF INDOLE COMPOUNDS TO INDOLINE COMPOUNDS

[75] Inventors: Bruce E. Maryanoff, Solebury Township, Bucks County; David F. McComsey, Philadelphia, both of Pa.

[73] Assignee: McNeil Laboratories, Incorporated, Fort Washington, Pa.

[21] Appl. No.: 867,564

[22] Filed: Jan. 6, 1978

[51] Int. Cl.$^2$ .................. C07D 209/04; C07D 209/94; C07D 487/04
[52] U.S. Cl. ........................ 260/326.11 R; 260/315; 260/326.9; 562/605; 260/347.3
[58] Field of Search ... 260/326.11 R, 315 (U.S. only), 260/326.9

[56] References Cited

U.S. PATENT DOCUMENTS

| | | | |
|---|---|---|---|
| 2,569,415 | 9/1956 | Hartmann et al. | 548/336 |
| 3,329,619 | 7/1967 | Hudson et al. | 252/148 |
| 3,657,254 | 4/1972 | Barkov et al. | 260/293.55 |
| 3,853,878 | 12/1974 | Jonas et al. | 260/326.11 R |
| 3,980,797 | 9/1976 | Jonas et al. | 424/274 |

OTHER PUBLICATIONS

Lane et al., J. Org. Chem. 39, 3052–3054 (1971).
Yoon et al., J. Org. Chem. 38, 2786–2792 (1973).
Brown et al., J. Am. Chem. Soc. 92 (6), 1637–1646 (1970).
Pelter et al., Chem. Comm., 1970, pp. 347–348.
Lane, Chem. Reviews 76, 773–779 (1976).
Littell et al., J. Org. Chem. 38, 1504–1510 (1973).
Kikugawa et al., J. Chem. Research (S), 212–213 (1977).
Berger et al., J. Med. Chem. 20, 600–601 (1977).
Brown et al., J. Am. Chem. Soc. 93 (7), 1816–1818 (1978).
Aldrich Catalog of Organic Chemicals, 1977–1978, pp. 109–110, 159.
Alfa/Ventron Catalog, pp. 6–9.
J. Organic Chem. 12/9/77 issue, back cover.
Kabalka et al., J. Org. Chem. 42, 512–517 (1977).
Robinson, Chem. Reviews 69, 785–797 (1969).
Brown et al., J. Am. Chem. Soc. 82, 681–686 (1960).
Gribble et al., J. Am. Chem. Soc. 96, 812–814 (1974).
Berger et al., Tetrahedron Letters, Nos. 22–23, 1807 (1975).
Monti et al., Tetrahedron 27, 3331–3339 (1971).
Plieninger et al., Liebig's Annalen Chem., 680, 69, 74–75 (1964).
Berger, Synthesis, 508–510 (1974).
Feuer et al., J. Org. Chem. 34, 1817–1821 (1969).
Brown et al., J. Am. Chem. Soc. 99, 25, 8218–8226 (1977).
Gribble et al., Synthesis, pp. 859–860 (1977).
Kikugawa, J. Chem. Research (S), 184–185 (1978).
Maryanoff et al., J. Org. Chem. 43, No. 13, 2733–2755 (1978).

*Primary Examiner*—Donald G. Daus
*Assistant Examiner*—Diana G. Rivers
*Attorney, Agent, or Firm*—Alice O. Robertson

[57] ABSTRACT

A method for reducing indole compounds to the corresponding indoline compounds substantially free of undesirable side reactions is described. The method involves contacting an indole compound with a borane complex reagent in the presence of trifluoroacetic acid. The method is rapidly and readily carried out and provides an excellent method for preparing certain indoline compounds from the corresponding indole compounds. A novel dioxyborane useful as a borane reagent is also disclosed.

12 Claims, No Drawings

REDUCTION OF INDOLE COMPOUNDS TO INDOLINE COMPOUNDS

BACKGROUND OF THE INVENTION

Compounds having an indoline nucleus in their structure are of interest for their biological and pharmacological properties. Many demonstrate neuroleptic, antidepressant and other pharmacological and biochemical properties and may be active ingredients in such compositions (e.g., U.S. Pat. Nos. 3,980,797, 3,657,254, 2,569,415); some are taught to be useful in non-biological compositions, such as, for example, in ferrous metal pickling compositions (U.S. Pat. No. 3,329,619). In view of their pharmacological and biochemical properties, they also are of interest for experimental purposes such as in studies relating structure to activity. Of particular pharmacological and biochemical interest are indolines which have another basic nitrogen function in their molecular structure, most especially those having an aminoalkyl group. The basic nitrogen function may be part of a heterocyclic ring joined to the pyrrolic, the benzenoid or to both pyrrolic and benzenoid rings. By "pyrrolic" as herein employed is meant the five-membered heterocyclic portion without regard to whether it is in the pyrrole form as an indole or in the reduced form as an indoline.

Frequently, an indole nucleus containing compound is available or its preparation substantially more facile. Under such circumstances it is desirable to be able to directly reduce the indole to the corresponding indoline. Attempted reductions of compounds with an indole nucleus have met with varying results when known procedures were employed. Reductions of those indoles having an aminoalkyl group either as a side chain or as part of a condensed ring are difficult and it has been especially so when there is at least one hydrogen on the aminoalkyl nitrogen. Moreover, a method for the selective reduction of the pyrrolic ring is desirable in studies connected with the indole alkaloids.

The reduction of indoles to obtain the corresponding indolines has been attempted with various reagents such as metal-acid, hydrogen plus catalyst, metal hydrides, metal borohydrides and boranes. These have been summarized in a review article by B. Robinson in Chem. Review 69, 785 (1969). The reported results vary from no reduction, reduction of the pyrrolic ring, reduction of the benzenoid ring, reduction of functional groups, to reduction resulting in ring rupture, with more than one type of reduction frequently occurring.

One group of reagents discussed are metal borohydrides and boranes. Although boranes and metal borohydrides were once considered together as boron reagents, they are now recognized as being non-analogous. The difference between the reducing capability of a borane reagent and a metal borohydride reagent has been explained by H. C. Brown et al (J. Am. Chem. Soc. 82, 681 (1960)) as the difference in the acidic and basic nature of the two reagents. In any event, they exhibit different reducing properties and are part of non-analogous systems. Thus, borane, as distinguished from borohydride, has been found by Brown et al as being a powerful reducing agent for functional groups such as aldehyde, ketone, epoxide, lactone, carboxylic acid, nitrile, acyl group and t-amide groups.

The use of metal borohydrides on indole has been found by Gribble et al (J. Am. Chem. Soc. 96, 812 (1974)) to accomplish reduction in the pyrrolic ring but with different results depending on the particular combination of acid and borohydride and depending on the substrate indole compound. Most frequently, the reduction was accompanied by alkylation at the indole nitrogen; in fact, the combination of metal borohydride and carboxylic acid is suggested by Gribble for alkylation of aromatic amines. Indeed, our attempts to reduce certain aminoalkyl substituted indoles with metal borohydride were accompanied by alkylation at the amino nitrogen or at the pyrrolic nitrogen if the indole compound did not have a substitutable basic function.

The use of borane reagents on indole nucleus containing systems as reported by various workers show variable results (J. G. Berger et al., Tetrahedron Letters Nos. 22 and 23, 1807 (1975); S. A. Monti et al., Tetrahedron, 27, 3331 (1971); H Plieninger et al., Liebigs Ann. Chem. 680, 69 (1964); J. G. Berger, Synthesis, 508 (July, 1974)); H. Feuer et al., J. Org. Chem. 34, 1817 (1969); and R. Littell et al., J. Org. Chem. 38, 1504 (1973)). None of these report successful reduction to the corresponding indoline of an indole compound which has an alkylatable basic nitrogen such as a hydrogen bearing aminoalkyl group.

In view of the absence of a reliable method for reducing an indole compound having a basic nitrogen containing substituent, particularly an alkylatable aminoalkyl substituent, and further since attempts to carry out such reduction with the most promising of the art processes were unsuccessful, it is an object of the present invention to provide an improved, more generally applicable and more reliable procedure for reducing compounds having an indole nucleus to the corresponding indoline compounds, especially indole compounds having a basic nitrogen function, and most especially an alkylatable aminoalkyl substituent. It is a further object to provide a method for preparing in good yields, indoline compounds having an aminoalkyl substituent from the corresponding indole compounds, most particularly those indoline compounds which have at least one hydrogen on the amino nitrogen of the aminoalkyl group. It is a still further object to provide a method in which the product could be obtained substantially free of alkylation products. Other objects and advantages of the present invention will be apparent from the following description of the invention.

STATEMENT OF THE INVENTION

According to the present invention it has been discovered that an indole compound may be reduced to the corresponding indoline compound rapidly and in good yields with a borane reagent in the presence of trifluoroacetic acid. The process provides a means for producing certain indoline compounds from the corresponding indole compounds not heretofore readily possible. The composition of borane reagent in trifluoroacetic acid suitable for carrying out this process also constitutes an aspect of this invention.

DESCRIPTION OF THE INVENTION

An indole compound as hereinafter defined may be reduced without significant undesirable side reactions to the corresponding indoline compound by contacting the indole compound with a borane reagent as hereinafter defined in the presence of trifluoroacetic acid. By carrying out the reduction reaction employing the combination of borane reagent and trifluoroacetic acid, the reaction proceeds substantially instantaneously, or in any event, very rapidly and at low temperatures so that the need for long reaction time or for heating is completely avoided. Moreover, the reaction produces good yields of the corresponding indoline product.

Surprisingly, trifluoroacetic acid appears to be uniquely useful in this reaction with boranes. Thus, when trichloroacetic acid or difluoroacetic acid is substituted for trifluoroacetic acid, it is found that under similar conditions, the reaction proceeds poorly, i.e., in low yields and with formation of significant amounts of by-products. Further, unlike some reported reactions in which the use of trifluoroacetic acid, or other carboxylic acids, with metal borohydride has been found to foster significant alkylation of the pyrrolic nitrogen, alkylation has been negligible within the time required for complete reduction of the indole in the process of the present invention. Similarly, where the indole compound is one having an aminoalkyl or basic group with at least one hydrogen, there also has been no significant alkylation of said basic nitrogen within the reduction period. The present process is further advantageous in providing a homogeneous reaction medium for ammonium salts which form from indoles bearing a basic nitrogen when acid is added to the reaction medium. The present process is further advantageous in avoiding the necessity of using strongly basic reagents such as metal borohydrides and particularly of materials susceptible to releasing hydrogen cyanide on acidification during the course of reaction or during work up such as sodium cyanoborohydride.

The expression "indole compound" as herein employed is intended to embrace compounds which have an indole nucleus

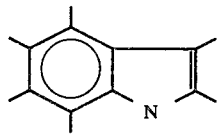
(I)

which may not only be substituted (except as hereinafter limited) but which may be part of a condensed or fused ring system. Thus, some of the free valences in the foregoing benzenoid and pyrrolic rings may form part of another ring. The scope is limited only by the indole compound being one capable of forming an indolenium ion in the trifluoroacetic acid containing reaction medium. Thus, the process is applicable to indole compounds which do not have electron withdrawing groups, such as carbalkoxy and phenyl, substituted directly on the 2-position. Other common electron withdrawing groups which should be avoided on the 2-position include ketone, aldehyde, nitrile, carboxamide and carboxy. Groups which should be avoided elsewhere in the compound include ketone, aldehyde, carboxy, hydroxy, thiol, acetylene, epoxide and imine. Groups which may be substituted elsewhere in the compound include amine, ester, amide, nitrile, halogen, alkoxy, thioalkoxy, amidine, nitro and sulfone. The presence of an olefin linkage is permissible when the borane reagent as hereinafter fully defined is dioxyborane but is to be avoided when it is a borane complex as hereinafter more fully defined.

While the presence of a benzenoid ring in the form of a phenyl substituent as in 2-phenylindole is to be avoided, the presence of such a ring as part of a condensed ring system is not. Thus, carbazole, substituted carbazole, and higher condensed systems are within the scope of the expression "indole compound."

The expression "indoline compound" as herein employed is intended to embrace compounds in which the pyrrolic ring is a reduced ring corresponding to indoline but which otherwise may include substituted and condensed rings as above defined for indole compounds. The indoline compounds may be represented by the formula

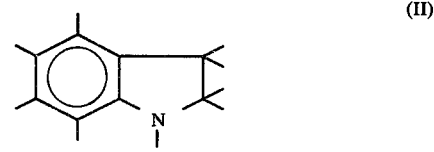
(II)

The reaction is particularly useful for the reduction of indole compounds having a basic nitrogen group. The basic nitrogen is most frequently an amino group but includes others and may be attached directly to the indole nucleus or may be attached through a side-chain. Moreover, the basic nitrogen containing group may be attached to the pyrrolic ring, the benzenoid ring or both. The reaction is especially useful for the reduction of aminoalkyl substituted indoles in which the aminoalkyl group is attached to the pyrrolic nucleus and represented by

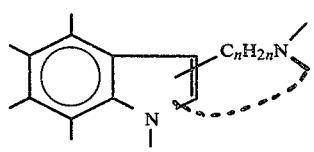
(Ia)

and most especially useful for aminoalkyl substituted indole compounds in which the aminoalkyl substituent is primary or secondary, i.e., there is at least one hydrogen on the aminoalkyl (non-pyrrolic) nitrogen as represented by

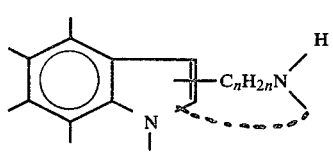
(Ib)

In the foregoing Formula Ia and subsequent formulas, n is preferably an integer of from about 1 to 4. As can be seen from the foregoing, the aminoalkyl group may be attached to any of the positions in the hetero or pyrrolic ring of the indole nucleus. Thus, it may be attached to nitrogen at the No. 1 position or to carbon at the No. 2 or No. 3 position. In addition to compounds in which the aminoalkyl group is part of a side-chain, as suggested by the dotted line the aminoalkyl group may be part of a condensed cyclic nucleus and when part of a ring, the indole compound may be represented by Formulas Ic and Id

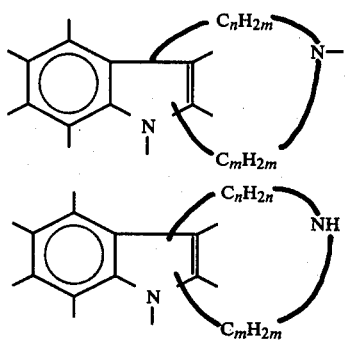

(Ic)

(Id)

In the foregoing and subsequent formulas, m is also an integer of from about 1 to 4, provided that the sum of $C_mH_{2m}$ and $C_nH_{2n}$ taken with the non-pyrrolic nitrogen atom and the atoms from the pyrrolic nucleus will form a ring of from about 5 to 8 atoms. The sum of m and n will usually be from 2 to 6.

The various indole compounds having a basic nitrogen groups which may be reduced by the process of the present invention may be illustrated with the following structural formulas as merely representative.

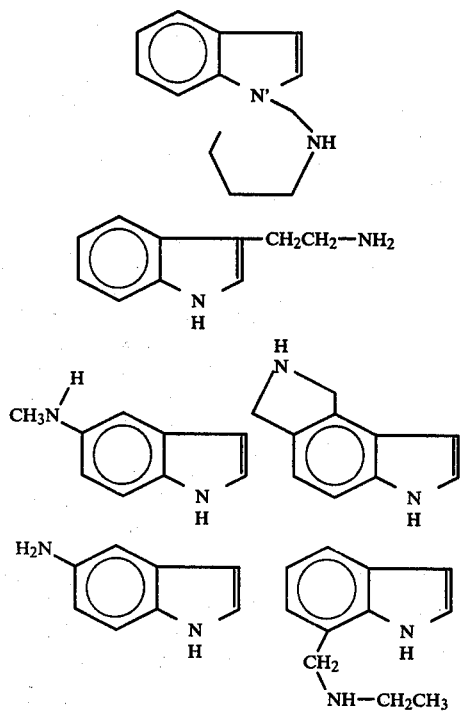

The indoline compounds for which the process provides a particularly useful method of synthesis are compounds represented by Formulas IIa and IIb

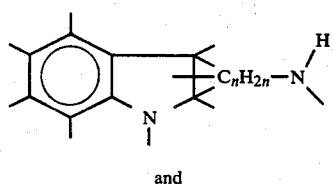

(IIa)

and

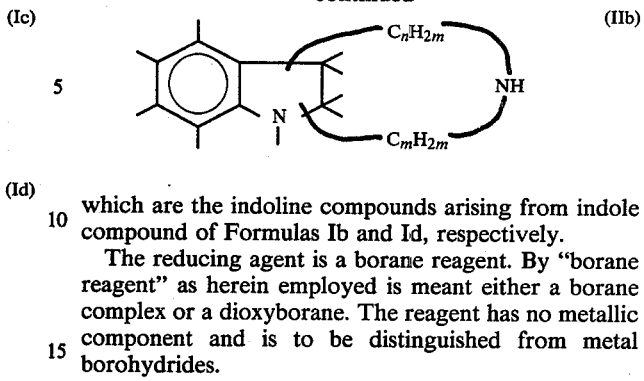

(IIb)

which are the indoline compounds arising from indole compound of Formulas Ib and Id, respectively.

The reducing agent is a borane reagent. By "borane reagent" as herein employed is meant either a borane complex or a dioxyborane. The reagent has no metallic component and is to be distinguished from metal borohydrides.

Borane complexes are neutral complexes of $BH_3$ (Lewis acid) with a Lewis base, such as an ether or an amine, and many are well known. The preferred complexes are borane.tetrahydrofuran ($BH_3$.THF) and borane.pyridine ($BH_3$.Py). Other borane complexes may be employed include borane.dimethylsulfide, borane.trimethylamine, borane.lutidine, borane.collidine, borane.morpholine, borane.phenylmorpholine, and the like. Factors affecting choice of reagent include the nature of the substrate as well as effectiveness of the reagent or anticipated difficulty or ease in isolation of the product. Thus, for example, when the substrate is an indole having a substituent containing a basic nitrogen, borane.trimethylamine is less preferred as a reagent.

Dioxyboranes are compounds of borane with acid hydroxy compounds or carboxylic acids and which may be represented by

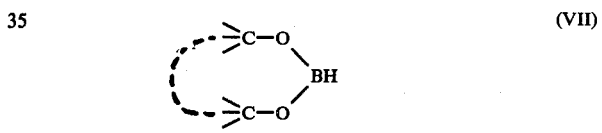

(VII)

The preferred dioxyborane for the present process is catechol.borane

(VIII)

A dioxyborane is also found to arise by the interaction of a borane complex and trifluoroacetic acid. Such dioxyborane when the borane complex is $BH_3$.THF may be represented by

(IX)

The formation of such dioxyborane was substantiated by the addition of $BH_3$.THF to excess trifluoroacetic acid in the absence of indole and observing the evolution of two equivalents of hydrogen and the generation of a substance stable to trifluoroacetic acid but decomposed by water with the evolution of additional hydrogen. Spectral evidence (ir, $^1$Hnmr, $^{11}$Bnmr) supported its formation. Such dioxyborane would be formed in one of the procedures for carrying out the present invention in which a borane complex is first contacted with trifluoroacetic acid. Thus, a novel dioxyborane is also an agent in the present process.

Many suitable borane reagents are commercially available, oftentimes as solutions in an inert solvent such as, for example, tetrahydrofuran, hexane, methylene chloride and the like. The borane reagents which are not available commercially may be prepared by methods described in the art, particularly "Boranes in Organic Chemistry" by H. C. Brown, 1972, Cornell University Press. The catechol borane (also identified as 1,3,2-benzodioxaborole) is described in the article by Brown et al in J. Am. Chem. Soc. 93, 1816 (1971).

Borane reagents which are available in solution may be employed as the solutions. The borane reagents which are liquid may be employed neat. Those which are solids are preferably employed in an inert solvent such as tetrahydrofuran, hexane, methylene chloride and the like. Thus, it is preferable to employ the borane reagent in a liquid form, whether neat or in solution, and the expression "liquid form" is intended to embrace a solution as well as the normal physical state of the borane reagent.

Trifluoroacetic acid has been found to be uniquely useful for producing the desired results of rapid reaction and high yields not achieved by other polyhaloacetic acids, such as trichloroacetic acid or even difluoroacetic acid. Thus, $BH_3$.THF employed with trichloroacetic acid or difluoroacetic acid produced poor results under similar conditions. Commercial anhydrous trifluoroacetic acid has been found to be satisfactory in the present process.

The borane reagent is employed in molar excess. From about 1.5 to 5 moles of borane reagent for each mole of indole compound may be employed; generally, from 2 to 3 moles of reagent for each mole of indole compound is preferred. It has been found that when employing 1 M $BH_3$.THF in tetrahydrofuran, it is desirable to employ a molar ratio of borane reagent:indole compound of 3:2 for efficient and rapid reduction. The trifluoroacetic acid is employed in excess, in amounts sufficient to function as a solvent for the indole compound and to provide for loss of the acid by interaction with borane complex.

The reaction is carried out in an inert atmosphere and under substantially anhydrous conditions. The inert atmosphere is conveniently provided by nitrogen gas, although argon and the like may be employed. Because of the hygroscopic nature of trifluoroacetic acid, absolute anhydrousness is not usually achieved; however, since addition of even a drop of water into the reaction mixture will destory the borane reagent, adequate care should be taken to maintain substantially anhydrous conditions.

The reaction takes place on contacting the reactants in the presence of trifluoroacetic acid (TFA) in an inert atmosphere. The reaction is preferably carried out with cooling so that the temperature is maintained in the range of about 0° to 25° C. No heating is necessary. The reaction is rapid, generally substantially complete within a few minutes, and provides high yields of the desired products. Usually stirring is continued for about 15 minutes to insure completion of reaction; stirring with cooling may be continued for longer periods without observable detriment in most cases. The progress of the reaction may be determined by sampling the reaction mixture and subjecting the sample to gas liquid chromatographic analysis (GLC). The order of addition usually is not critical. For most compounds good results are obtained by any of the methods described below. For acid sensitive indoles, the procedure hereinafter referred to as the reverse addition procedure is the method of choice. The choice of procedure may be merely a matter of convenience.

In the preferred method for carrying out the reaction, the appropriate indole compound first is dissolved in trifluoroacetic acid with stirring under an inert atmosphere and the resulting solution cooled in an ice bath. Thereafter, the borane reagent in liquid form is added dropwise at such a rate that excessive foaming from the generated hydrogen or excessive temperature elevation is avoided. The temperature of the reaction mixture generally is maintained in the range of 0° to 25° C. but may be as high as 50° C.; preferably the initial temperature is continued for a few minutes after completion of the addition. A sample may be taken for GLC analysis or the stirring may be continued for about 15 minutes, one-half hour, or longer. After completion of the reaction, water is added slowly and the reaction mixture stirred at room temperature to decompose excess reagent until no further evolution of hydrogen is noted. The solution is then evaporated under reduced pressure to remove the volatile solvent or solvents, and to obtain a mixture of the indoline compound product as an acid addition salt with TFA, and residual water and solvent or solvents. The product is recovered from the reaction mixture employing conventional procedures. For example, the mixture is made basic with an aqueous sodium hydroxide solution, the basic mixture extracted with a water-immiscible organic solvent (e.g., methylene chloride, carbon tetrachloride, etc.) to obtain the desired indoline compound in the organic solution, the organic solution dried, and the solent then vaporized from the organic solution to recover the desired indoline compound as residue.

In another procedure for carrying out the reaction, trifluoroacetic acid is added last. This procedure is the preferred procedure for acid sensitive indoles and will be referred to as the "reverse addition" procedure. In this procedure, the appropriate indole compound is dissolved in a solution of borane reagent in an inert solvent such as tetrahydrofuran with stirring and cooling in the temperature range of about 0° to 25° while maintaining an inert atmosphere. To the mixture still while cooling, trifluoroacetic acid is added dropwise with stirring whereupon a reaction takes place with the formation of the indoline compound. The reaction by this modification also is complete in a very short time but the stirring may be continued for several minutes or more to insure completion of the reaction. After completion of the reaction, the excess reagent is decomposed by the addition of water and the product recovered from the reaction mixture in a manner as previously described.

In still another procedure, a borane reagent is dissolved with stirring in trifluoroacetic acid while maintaining an inert atmosphere and temperature of about 0° to 20° C. The mixture is cooled in an ice bath at about 5° C. and a solution of the indole compound, preferably in an inert solvent, added thereto in a portionwise manner. The stirring and reaction is continued for at least several minutes, and sometimes for several hours, to insure completion of the reaction. As a result of these operations, the desired indoline product is formed in the reaction mixture. Thereafter the product is recovered from the reaction mixture in a manner similar to that previously described.

By the process of the present invention, namely of causing an indole compound to react with an borane reagent in the presence of trifluoroacetic acid, good yields of indoline compound have been possible within a very short time and without the necessity for application of heat. The progress of the reaction can be determined readily as previously noted by sampling the reaction mixture and analyzing the sample by GLC analysis after completion of the addition. It has been found that by employing the process of the present invention, good yields of the indoline compound product is found to have been formed substantially instantaneously and that the product is recoverable with only the deiminution in yield expected on work-up. This is in contrast to other methods where GLC analyses indicate low yields or even absence of the desired indoline product in the reaction mixture. Thus, not only has a novel synthetic method become available for basic nitrogen substituted or aminoalkyl indolines but a method is provided which is also useful for preparation of indoline compounds previously obtained in poor yields from the corresponding indole compounds.

The stereochemistry of the reduction appears to be dependent on the nature of the substituent on the pyrrolic ring. When a six-membered ring is fused onto the pyrrolic ring, cis reduction is generally obtained whether or not the said fused ring is carbocyclic or heterocyclic. Thus, for these compounds, a stereospecific means for producing the compounds is achieved. When the indole compound is unfused, e.g., 2,3-dimethyl indole, or where the fused ring is larger than six, mixtures of configurational products are obtained.

The present process is particularly useful as a needed method of synthesis of an indoline compound having a basic nitrogen bearing group represented by the formula

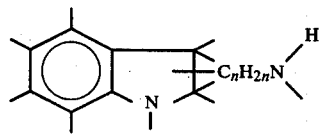

from the corresponding indole compound.

The following examples illustrate the invention but are not to be construed as limiting:

EXAMPLE I

2,3,4,5,11,11a-HEXAHYDRO-1H-[1,4]-DIAZEPINO[1,2-a]INDOLE

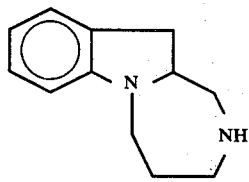

70 milligrams of 2,3,4,5-tetrahydro-1H-[1,4]-diazepino [1,2-a]indole (prepared as described in U.S. Pat. No. 3,867,374) was dissolved in 3 milliliters of trifluoroacetic acid and the mixture was stirred for 10 minutes under nitrogen. Thereafter, 1.5 milliliters of a 1 M solution of $BH_3.THF$ in tetrahydrofuran was added dropwise with stirring and the resulting mixture stirred for 40 minutes to obtain a 2,3,4,5,11,11a-hexahydro-1H-[1,4]-diazepino[1,2-a]indole product in the reaction mixture. Water (0.5 milliliter) then was added dropwise to the mixture cooled in an ice bath, followed by 10 percent NaOH until pH tested about 9 (pH test paper). The alkaline solution was extracted with methylene chloride and the methylene chloride solution washed with saturated sodium chloride solution and dried over potassium carbonate. The dried solution was filtered to remove the drying agent and evaporated in vacuo to obtain 60 milligrams (85 percent yield) of 2,3,4,5,11,11a-hexahydro-1H-[1,4]diazepino[1,2-a]indole product as an oil having NMR and mass spectra appropriate for the compound. The hydrochloride salt of the product melted 238°–240° C.

EXAMPLE II 50 milligrams of 2,3,4,5-tetrahydro-1H-[1,4]-diazepino [1,2-a]indole was dissolved in 1 milliliter of trifluoroacetic acid under nitrogen and the solution stirred 5 minutes while cooling in an ice bath. To the solution was added dropwise 0.10 milliliter of borane-pyridine complex with continued stirring and cooling under nitrogen.

A gas chromatographic analysis of a sample taken about one minute after completion of the addition showed reduction to be substantially complete (substantially complete conversion and absence of indole-originating by-products) with the formation of 2,3,4,5,11,11a-hexahydro-1H-[1,4]-diazepino[1,2-a]indole product. It was noted that a by-product tended to be formed between the borane complex and trifluoroacetic acid which increased with time.

EXAMPLE III 45 milligrams of 2,3,4,5-tetrahydro-1H-[1,4]-diazepino [1,2-a]indole was dissolved in 1.0 milliliter of trifluoroacetic acid under nitrogen and stirred for 5 minutes. The solution was cooled in an ice bath and 0.12 milliliter of catecholborane was added dropwise with continued stirring under nitrogen.

Gas chromatographic analyses of samples taken at about 2 minutes and 26 minutes after completion of the addition showed complete reductive conversion to the 2,3,4,5,11,11a-hexahydro-1H-[1,4]-diazepino[1,2-a]indole product and absence of indole-originating and/or solvent-originating by-products.

The reaction solution was worked up by addition of water, stirring for several minutes, basifying with 10 percent sodium hydroxide to pH>10 and extracting with methylene chloride. The methylene chloride solution as dried over potassium carbonate, filtered and evaporated in vacuo to produce 78 percent (isolated) yield of the 2,3,4,5,11,11a-hexahydro-1H-[1,4]-diazepino[1,2-a]indole product which was shown to be homogeneous by GLC.

EXAMPLE IV

The results on the yield of 2,3,4,5,11,11a-hexahydro-1H-[1,4]-diazepino[1,2-a]-indole obtainable from 2,3,4,5-tetrahydro-1H-[1,4]-diazepino[1,2-a]indole by varying the reducing agent system, i.e., borane reagent and/or acid, but otherwise carrying out the reaction in a manner similar to that described in Examples I–III (and including the results of Examples I–III) are seen in Table I

TABLE I

| Reducing Agent System | Yield* |
|---|---|
| BH$_3$ . THF in TFA | 80–86 percent |
| BH$_3$ . THF (no TFA) | No reaction |
| BH$_3$ . THF in CCl$_3$COOH | Poor reaction; about 20 percent |
| BH$_3$ . THF in CHF$_2$COOH | About 40 percent |
| BH$_3$ . Py in TFA | 90 percent |
| Catechol-Borane in TFA | 80 percent |
| BH$_3$ . N(CH$_3$)$_3$ in TFA | Incomplete reaction; 20 percent |
| BH$_3$ . S(CH$_3$)$_2$ in TFA | 84 percent |

*Yield based on work up within one hour by recovering crude product as residue, determining amount of desired product by GLC and characterizing the product by spectrometry.

EXAMPLE V

2-(3-INDOLINYL)ETHYLAMINE 2-(3-Indolyl)ethylamine in an amount of 9.4 grams (58.8 millimoles) was dissolved in 120 milliliters of trifluoroacetic acid under nitrogen. The solution was cooled in an ice bath and 100 milliliters of about 1 M BH$_3$.THF in tetrahydrofuran solution was added slowly over about 30 minutes. Thereafter, water (50 milliliters) was added, the resulting solution stirred at room temperature for about 75 minutes, and then evaporated in vacuo to about 40 milliliters of a semi-solid viscous oil. The oil was partitioned between methylene chloride and aqueous sodium hydroxide solution (pH > 10). The organic layer was dried over potassium carbonate, filtered and evaporated in vacuo to obtain 8.6 grams of a yellow oily 2-(3-indolinyl)ethylamine product of 98 percent purity (by gas layer chromatographic analysis) in a 90 percent isolated yield. NMR was appropriate for the compound. The HCl salt of 2-(3-indolinyl)ethylamine had a melting point of 186°–188° C.

EXAMPLE VI

1,2,3,4,4a,9a-HEXAHYDROCARBAZOLE 1,2,3,4-Tetrahydrocarbazole (75 milligrams) was dissolved under nitrogen in 3 milliliters of trifluoroacetic acid. To the mixture, cooled in a water bath, was added dropwise about 1.5 milliliters of an about 1 M BH$_3$.THF in tetrahydrofuran. The mixture was stirred at room temperature for about 45 minutes. Thereafter, water (1 milliliter) was added slowly and the resulting solution stirred for 10 minutes. The solution was then made basic with 10 percent aqueous sodium hydroxide, and the basic solution extracted with methylene chloride. The organic methylene chloride layer was washed once with saturated sodium chloride, dried over potassium carbonate, and evaporated in vacuo to obtain 60 milligrams (80 percent yield) of a crystalline 1,2,3,4,4a,9a-hexahydrocarbazole product, m.p., 93°–96° C.

EXAMPLE VII

A summary of the wide variety of different structural configurations to which the reaction is applicable when carried out by adding borane reagent to a solution of an indoline compound in trifluoroacetic acid in a manner similar to that described in the foregoing examples, is seen in Table II where the indoline compound products and yields are listed. The yields are yields of isolated products. Generally where the isolated material was not completely pure, the yield value was determined by comparing with an authentic standard for extent of purity by GLC and characterized by spectrometry in the manner indicated in the footnotes. The yield values in parentheses are GLC determined yield of product in the reaction mixture. The table includes the three compounds described in the preceding examples.

TABLE II

| INDOLINE COMPOUND* | YIELD |
|---|---|
| (hexahydrocarbazole structure) | 80% (90%); one isomer |
| (indoline with NH side chain) | 86% (98%) |
| (3-(2-aminoethyl)indoline, CH$_2$CH$_2$NH$_2$) | 86% |
| (5-nitroindoline) | (1) (70%) + dimer of indole |
| (5-methoxy hexahydrocarbazole, CH$_3$O) | (2) 90%, one isomer |
| (2-methylindoline, CH$_3$) | (3) 88% |
| (N-phenethyl hexahydrocarbazole, N—CH$_2$CH$_2$φ) | (4) 70% |
| (2,2-dimethylindoline, CH$_3$, CH$_3$) | (5) 82% > 2:1 trans epimer |
| (5-methyl, NCH$_3$ hexahydrocarbazole) | (6) 80%; 1 isomer |
| (cyclooctane-fused indoline) | (7) 80%; 2.5:1 ratio of isomers |
| (1-cyanomethylindoline, CH$_2$CN) | (8) 58% |

TABLE II-continued

| INDOLINE COMPOUND* | YIELD |
|---|---|
| 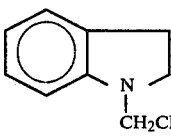 | (9) 45% |

*Characterizations of the products were by m.p. of compound, m.p. of derivative or spectra. Spectral characterizations include comparison with authentic sample, comparison with literature values and/or assignment of structure based on original spectroscopic data as indicated:
(1) NMR (comparison with commercial 5-nitroindoline;
(2) NMR and mass spectra (original data) and UV (J. R. Chalmers et al., J. Chem. Soc. 1115 (1957));
(3) NMR (CH₃, doub 1.25, J ~ 6Hz);
(4) NMR and mass spectra (original); m.p. of N-propionyl derivative, 110–112° C. (lit. m.p. 109–110° C., J. Med. Chem. 600, 20 (1977));
(5) NMR (F. A. Anet et al., Chem. and Ind. Jan. 12, 1963, 81);
(6) Mass spectra (original)., m.p. 260–265° C. (lit. m.p. 274–276, U.S. Pat. No. 3,657,254);
(7) Mass spectra (original); NMR (J. Org. CHem., 36, 2823 (1971));
(8) and (9) mass spectra (original).

EXAMPLE VIII

In an operation carried out in a manner similar to that described in Example II, 50 milligrams of 2-(3-indolyl)ethylamine is dissolved in 1.0 milliliter of trifluoroacetic acid under nitrogen atmosphere. The solution is cooled in an ice bath and 0.2 milliliter of borane-pyridine complex is added dropwise to the reaction mixture. After completion of the addition, stirring is continued for about 15 minutes to insure completion of the reaction with the formation of 2-(3-indolinyl)ethylamine product. The product is recovered from the reaction mixture in a manner similar to that previously described.

EXAMPLE IX

In an operation carried out in a manner similar to that described in Example II, [4aα,9bα]-2,8-dimethyl-2,3,4,4a,5,9b-hexahydro-1H-pyrido[4,3-b]indole may be obtained by the reduction of 2,8-dimethyl-2,3,4,5-tetrahydro-1H-pyrido[4,3-b]indole employing borane.-pyridine and trifluoroacetic acid.

EXAMPLE X

In operations carried out in a manner similar to that described in Example II, the following indole compounds may be reduced to the corresponding indoline compounds with borane.pyridine in trifluoroacetic acid:

2-Methylindole
2,3-Dimethylindole
1,2,3,4-Tetrahydrocarbazole
6-Methoxy-1,2,3,4-tetrahydrocarbazole
5-Nitroindole
1-Cyanomethylindole
5-Aminoindole
5-Methylaminoindole
7-(Ethylaminomethyl)indole

EXAMPLE XI

In an operation carried out in a manner similar to that described in Example III, 50 milligrams of 2-(3-indolyl)ethylamine is dissolved in 1.0 milliliter of trifluoroacetic acid under nitrogen atmosphere. The solution is cooled in an ice bath and 0.2 milliliter of catechol-borane is added dropwise to the reaction mixture. After completion of the addition, stirring is continued for about 15 minutes to insure completion of the reaction with the formation of 2-(3-indolinyl)ethylamine product. The product is recovered from the reaction mixture in a manner similar to that previously described.

EXAMPLE XII

In operations carried out in a manner similar to that described in Example III, [4aα,9bβ]-2,8-dimethyl-2,3,4,4a,5,9b-hexahydro-1H-pyrido[4,3-b]indole may be obtained by reduction of 2,8-dimethyl-2,3,4,5-tetrahydro-1H-pyrido[4,3-b]indole with catechol.borane in trifluoroacetic acid.

EXAMPLE XIII

In operations carried out in a manner similar to that described in Example III, the following indole compounds may be reduced to the corresponding indoline compounds with catechol-borane in trifluoroacetic acid:

2-Methylindole
2,3-Dimethylindole
1,2,3,4-Tetrahydrocarbazole
6-Methoxy-1,2,3,4-tetrahydrocarbazole
5-Nitroindole
1-Cyanomethylindole
5-Aminoindole
5-Methylaminoindole
7-(Ethylaminomethyl)indole

EXAMPLE XIV

2,3-DIHYDROINDOLE (Reverse Addition Method)

A. 75 milligrams of indole was dissolved in 1.5 milliliters of 1 M BH₃.THF solution in tetrahydrofuran by stirring under nitrogen while cooling in an ice bath and the stirring continued for about 5 minutes. Thereafter, 1.0 milliliter of trifluoroacetic acid was added dropwise with continued stirring, cooling and maintaining a nitrogen atmosphere. (Gas chromatographic analysis of a sample taken and isolated at this point indicated reaction to be complete in less than 1 minute.) Water (0.1 milliliter) was added to the mixture, followed by 10 milliliters of methylene chloride and then a sufficient amount of aqueous sodium hydroxide solution to bring the solution to a pH>9. The solution then was stirred about 15 minutes and a sample taken for gas chromatographic analysis. Analysis using an internal standard (commercial indoline) showed an 84 percent yield of 2,3-dihydroindole.

B. Gas chromatographic analysis of a sample obtained by mixing 75 milligrams of indole and 1.5 milliliters of 1 M BH₃.THF in tetrahydrofuran under nitrogen with cooling and then worked up without the addition of trifluoroacetic acid, showed only the presence of unreacted indole.

EXAMPLE XV

1-CYANOMETHYL-2,3-DIHYDROINDOLE

In an operation carried out in a manner similar to that described in Example XIV, 105 milligrams of 1-cyanomethyl indole was dissolved in 1.5 milliliters of 1 M BH₃.THF under nitrogen. Then, while cooling and stirring in an ice bath, 1.0 milliliter of trifluoroacetic acid was added dropwise to the indole-borane reagent mixture and after completion of the addition, stirring was continued for 1.5 hours while maintaining nitrogen atmosphere to obtain a 1-cyanomethyl-2,3-dihydroindole product in the reaction mixture. The product was recovered by adding first water, then methylene chloride, stirring the mixture (about 15 minutes), making alkaline (pH>9), separating the methylene chloride solution, drying the latter and evaporating the solvent from the dried solution in vacuo.

EXAMPLE XVI

In an operation employing 1 M $BH_3.THF$ as borane reagent and carried out in a manner similar to that described in Examples XIV and XV 2-(2,3-Dihydroindol-1-yl)ethylamine was obtained in about 65 percent yield from 2-(indol-1-yl)-ethylamine (as determined by GLC analysis and spectrometric characterization).

EXAMPLE XVII

In operations carried out in a manner similar to that described in Examples XIV–XVI, the following compounds may be prepared:

2,3,4,5,11,11a-Hexahydro-1H-[1,4]-diazepino[1,2-a]indole
2-(3-Indolinyl)ethylamine
1,2,3,4,4a,9a-Hexahydrocarbazole
5-Nitroindoline
2-Methylindoline

EXAMPLE XVIII

In an operation carried out in a manner similar to that described in Example I but employing 22 grams of 2,3,4,5-tetrahydro-1H-[1,4]-diazepino[1,2-a]indole, milliliters of 1 M $BH_3.THF$ in tetrahydrofuran and milliliters of trifluoroacetic acid, a 75 percent yield of 2,3,4,5,11,11a-hexahydro-1H-[1,4]-diazepino[1,2-a]indole was obtained as determined by GLC on the isolated product.

EXAMPLE XIX

In an operation carried out in a manner similar to that described in Example VI but employing $BH_3.S(CH_3)_2$ in tetrahydrofuran as the borane reagent, 1,2,3,4,4a,9a-hexahydrocarbazole was obtained 55 percent yield from 1,2,3,4-tetrahydrocarbazole as determined by GLC on the isolated product.

EXAMPLE XX

2,3,4,5,11,11a-HEXAHYDRO-1H-[1,4]-DIAZEPINO[1,2-A]INDOLE (Third Method)

About 1.5 milliliters of a 1 M $BH_3.THF$ solution in tetrahydrofuran and 3 milliliters of trifluoroacetic acid are mixed together and cooled in a water bath. To this mixture is added dropwise with cooling and under nitrogen atmosphere, 75 milligrams of 2,3,4,5-tetrahydro-1H-1,4]-diazepino[1,2-a]indole in about 3 milliliters of tetrahydrofuran. The addition is carried out in a dropwise manner and after completion of the addition stirring is continued for about 15 minutes to obtain a 2,3,4,5,11,11a-hexahydro-1H[1,4]-diazepino[1,2-a]indole product in the reaction mixture. Thereafter the product is isolated from the reaction mixture in a manner similar to that previously described to obtain a purified product.

EXAMPLE XXI

In operations carried out in a manner similar to that described in Example XX, the following compounds may be prepared:

2-(3-Indolinyl)ethylamine
2-(2,3-Dihydroindol-1-yl)ethylamine
[4aα,9bα]-2,8-Dimethyl-2,3,4,4a,5,9b,hexahydro-1H-pyrido[4,3-b]indole
5-Methylaminoindoline
2-(2,3-Dihydroindol-7-yl)ethylamine
1,2,3,4,4a,9a-Hexahydrocarbazole

EXAMPLE XXII

Preparation and Identification of Bis(trifluoroacetoxy)borane 5.7 Grams (0.05 mole) of trifluoroacetic acid in an equal volume of THF was placed under nitrogen atmosphere and cooled to 0° C. To the solution was added slowly and with stirring 25 milliliters of 1 M $BH_3.THF$. After completion of the addition, the mixture was allowed to warm to room temperature and the excess tetrahydrofuran evaporated in vacuo at 30° C. to recover a colorless oil as residue. A sample of the oil on addition to water caused evolution of hydrogen gas. The spectral data of the oil is as follows:

Ir $\nu$max CH stretching 2540 cm$^{-1}$ B-H (monomeric, non-bridged) 1780 cm$^{-1}$ C=O stretch $^1$Hnmr absorptions for complexed THF
The $^{11}$Bnmr on a solution in tetrahydrofuran and trifluoroacetic acid is $\delta + 2.5$ ppm downfield from $BF_3$.etherate.

The bis(trifluoroacetoxy)borane prepared as above-described is also suitable for use as a borane reagent according to the process of the present invention.

What is claimed is:

1. A process for selectively reducing an indole compound to the corresponding indoline compound which comprises causing an indole compound to react with a borane reagent in the presence of trifluoroacetic acid, said indole compound being characterized by having a basic nitrogen bearing group and also by the absence of an electron-withdrawing group substituted directly on the 2-position of the indole nucleus and thereby being one capable of forming an indolenium ion in the trifluoroacetic acid containing reaction medium, and said borane reagent being either (a) a neutral complex of $BH_3$ with an organic Lewis base and selected from the group consisting of $BH_3.THF$, $BH_3.Pyridine$ and $BH_3.S(CH_3)_2$ in THF, or (b) a dioxyborane represented by the structure

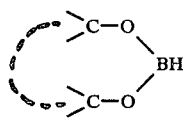

and selected from the group consisting of catechol borane, bis(trifluoroacetoxy)borane and a compound formed in situ from said complex of $BH_3$ with an organic Lewis base and trifluoroacetic acid.

2. A process according to claim 1 in which the indole compound having a basic nitrogen bearing group is an aminoalkyl substituted indole which may be represented by the structure

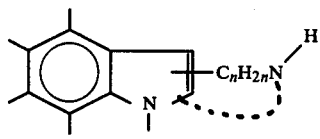

wherein n is an integer of from 1 to 4, inclusive.

3. A process according to claim 1 wherein the borane reagent is added to a solution of the indole compound in trifluoroacetic acid.

4. A process according to claim 1 in which the indole compound is added to a mixture of the borane reagent and trifluoroacetic acid.

5. A process according to claim 1 in which trifluoroacetic acid is added to a mixture of indole compound and borane reagent.

6. A process according to claim 1 in which the indole compound is one in which the basic nitrogen bearing group is an aminoalkyl group in an open chain configuration.

7. A process according to claim 6 in which the indole compound is 2-(3-indolyl)ethylamine.

8. A process according to claim 2 in which the basic nitrogen bearing group is an aminoalkyl group which is part of a ring condensed with the pyrrolic nucleus as represented by the formula

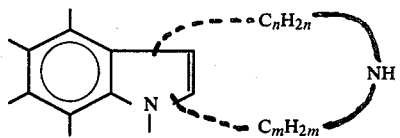

wherein m and n are integers of from 1 to 4 provided that the sum of $C_mH_{2m}$ and $C_nH_{2n}$ taken with the non-pyrrolic nitrogen atom and atoms from the pyrrolic nucleus for a ring of from 5 to 8 atoms.

9. A method according to claim 8 in which the indole compound is 2,3,4,5-tetrahydro-1H-[1,4]diazepino[1,2-a]indole.

10. A process for selectively reducing an indole compound to the corresponding indoline compound which comprises causing an indole compound to react with borane.tetrahydrofuran in the presence of trifluoroacetic acid, said indole compound being characterized by having a basic nitrogen bearing group and also by the absence of an electron-withdrawing group substituted directly on the 2-position of the indole nucleus and thereby being one capable of forming an indolenium ion in the trifluoroacetic acid containing reaction medium.

11. A process for selectively reducing an indole compound to the corresponding indoline compound which comprises causing an indole compound to react with borane.pyridine in the presence of trifluoroacetic acid, said indole compound being characterized by having a basic nitrogen bearing group and also by the absence of an electron-withdrawing group substituted directly on the 2-position of the indole nucleus and thereby being one capable of forming an indolenium ion in the trifluoroacetic acid containing reaction medium.

12. A process for selectively reducing an indole compound to the corresponding indoline compound which comprises causing an indole compound to react with catechol.borane in the presence of trifluoroacetic acid, said indole compound being characterized by having a basic nitrogen bearing group and also by the absence of an electron-withdrawing group substituted directly on the 2-position of the indole nucleus and thereby being one capable of forming an indolenium ion in the trifluoroacetic acid.

* * * * *